(12) United States Patent
Weeks

(10) Patent No.: US 6,794,374 B1
(45) Date of Patent: Sep. 21, 2004

(54) USE OF Δ5-ANDROSTENE-3β-OL7,17-DIONE IN THE TREATMENT OF ARTHRITIS

(75) Inventor: Charles E. Weeks, Battle Creek, MI (US)

(73) Assignee: Humanetics Corporation, Chanhassen, MN (US)

( * ) Notice: Subject to any disclaimer, the term of this patent is extended or adjusted under 35 U.S.C. 154(b) by 0 days.

(21) Appl. No.: 09/554,951

(22) PCT Filed: Nov. 17, 1998

(86) PCT No.: PCT/US98/24458

§ 371 (c)(1),
(2), (4) Date: Nov. 27, 2000

(87) PCT Pub. No.: WO99/25192

PCT Pub. Date: May 27, 1999

Related U.S. Application Data

(60) Provisional application No. 60/066,197, filed on Nov. 19, 1997.

(51) Int. Cl.[7] .............................................. A61K 31/56
(52) U.S. Cl. ..................................................... 514/178
(58) Field of Search ........................................ 514/178

(56) References Cited

U.S. PATENT DOCUMENTS

| | | | |
|---|---|---|---|
| 3,107,256 A | 10/1963 | Harnik | |
| 4,628,052 A | * 12/1986 | Peat | |
| 4,812,447 A | 3/1989 | Roberts | |
| 5,387,583 A | 2/1995 | Loria | |
| 5,585,371 A | * 12/1996 | Lardy | |
| 5,885,977 A | 3/1999 | Pauza et al. | |
| 6,667,299 B1 | 12/2003 | Ahlem et al. | ............... 514/178 |

FOREIGN PATENT DOCUMENTS

| | | |
|---|---|---|
| JP | 09151197 | 10/1997 |
| WO | WO 95/10527 | 4/1995 |
| WO | WO 97/37664 | 10/1997 |

OTHER PUBLICATIONS

The Merck Manual of Diagnosis and Therapy, 16th. ed., 1992, pp. 1293–1315, 1326–1327, 1338–1343, and 1369–1371.*

Mitchell, Eddie E., "Addressing the regio– and stereo–selectively seen in P4502A5 mutants with DHEA", dissertation in partial fulfillment of the requirements of the degree of Doctor of Philosophy at the University of Kentucky, Lexington, Kentucky (1996).

Su, Ching–Yuan, "Induction of hepatic mitochondrial glycerophosphate dehydrogenase and matic enzyme 1. Effects of Dehydroepiandrosterone 2. Effects of dehydroepiandrosterone–related steroids and cytochrome P–450 inducers", thesis submitted in partial fulfillment of the requirements of the degree of Doctor of Philosophy, University of Wisconsin–Madison, Madison, Wisconsin (1988).

Padgett, David Andrew, "Regulation of the immune system and its response to infection with dehydroepiandrosterone, androstenediol, and androstenetriol", dissertation submitted in partial fulfillment of the requirements for the degree of Doctor of Philosophy at Virginia Commonwealth University, Richmond, Virginia (1994).

Whitcomb, Jeannette Marie, "Effects of dehydroepiandrosterone, DHEA–analogs and food restriction on free radical reactions and autoimmunity in the MRL/1pr mouse", dissertation in partial fulfillment of the requirements of the degree of Doctor of Philosophy, Temple University, Ann Arbor, Michigan (1988).

* cited by examiner

*Primary Examiner*—Sreeni Padmanabhan
*Assistant Examiner*—San-ming Hui
(74) *Attorney, Agent, or Firm*—Daryl D. Muenchau

(57) ABSTRACT

Arthritis can be treated by administering therapeutic amounts of Δ5-androstene-3β-ol-7,17-dione and metabolizable precursors thereof, such a Δ5-androstene-3β-acetoxy-7,17-dione, which are readily metabolized in vivo to Δ5-androstene-3β-ol-7,17-dione but are not appreciably metabolizable in vivo to androgens, estrogens or dehydroepiandrosterone. Such treatment can be prophylactic, ameliorative or curative in nature.

21 Claims, No Drawings

USE OF Δ5-ANDROSTENE-3β-OL7,17-DIONE IN THE TREATMENT OF ARTHRITIS

This application claims the benefit of Provisional Application No. 60/066,197 filed Nov. 19, 1997.

FIELD OF THE INVENTION

This invention broadly relates to treatment strategies for arthritis. More specifically, the invention relates to prophylactic, ameliorative and curative drug therapies for arthritis.

BACKGROUND

Arthritis is a collective term for number of different conditions that cause pain, swelling and limited movement in joints and connective tissue throughout the body. Specific causes for arthritis are not yet known for most forms of the disease. The condition is usually chronic. The main symptoms of arthritis are joint pain, joint stiffness or inability to move a joint normally, and sometimes swelling that lasts more than two weeks. Most treatment programs include a combination of medication, exercise, rest, use of heat and cold, joint protection techniques, and sometimes surgery.

The three most prevalent forms of arthritis are osteoarthritis (OA), fibromyalgia (FM), and rheumatoid arthritis (RA).

Osteoarthritis (OA) is a degenerative joint disease characterized by a breakdown of the joint's cartilage. Cartilage functions to cushion the ends of the bones at each joint. A breakdown of the cartilage causes the bones to rub against each other, causing pain and loss of movement. OA primarily affects hands and weight-bearing joints, such as the knee, hips, feet and back. Risk factors for OA include advanced age, obesity, joint injury, and genetic disposition. Suggested causes for OA include an abnormal release of destructive enzymes from the cartilage cells themselves, and inherent defects in the way joints fit together. Most people over 60 suffer from OA, but only about one-third of those over 60 exhibit symptoms of OA.

Conventional treatment of OA focuses on decreasing pain and improving joint movement. Medications include aspirin, acetaminophen, ibuprofen and nonsteroidal anti-inflammatory drugs (herein after NSAIDs) for pain relief and inflammation reduction. Corticosteriod injection directly into affected joints in acute cases is also employed. Other noninvasive techniques commonly used to control OA include heat/cold treatment, exercise, joint protection and weight control.

Fibromyalgia (FM) is manifest as widespread pain affecting muscles and attachments to the bone. The patient may also exhibit tender points, specific areas that hurt when pressure is applied. Other symptoms can include fatigue, sleep disturbances, migraine headaches, irritated bowel syndrome, chest pain and nervous system symptoms such as depression.

Conventional treatment of FM include use of medications including aspirin, acetaminophen, ibuprofen or NSAIDs for pain relief and inflammation reduction.

Rheumatoid arthritis (RA) is an inflammatory disease having many components, including an autoimmune disorder aspect. The autoimmune disorder aspect is generally characterized by inflation of the membrane lining the joint resulting from an attack upon the joint by the body's own immune system. The inflammation cause pain, stiffness, warmth, redness and swelling. The inflamed joint lining, call the synovium, can invade and damage surrounding bone and cartilage. The involved joint can lose shape and alignment, resulting in pain, loss of movement and possible destruction of the joint. Early in the disease, people may notice general fatigue, soreness, stiffness and aching. Pain usually occurs in the same joints on both sides of the body and will usually start in the hands or feet. RA can also affect wrists, elbows, shoulders, neck, knees, hips and ankles. Other symptoms include lumps, called rheumatoid nodules, under the skin in areas subjected to pressure, such as the back of elbows.

RA can be diagnosed by a laboratory test for rheumatoid factor, an abnormal substance found in the blood of about 80% of adults with RA However the presence or absence of rheumatoid factor does not in itself indicate that one has RA. An overall pattern of symptoms, medical history and physical examination are also used in diagnosing RA.

Conventional treatment of RA focuses on reducing swelling, relieving pain and stiffness, and maintaining normal joint function. Medications include NSAIDs for controlling inflammation, joint pain, stiffness and swelling. Disease-modifying drugs include low doses of prednisone, methotrexate, hydroxychloroquine, azulfidine, gold salt and cyclosporin, used alone or in combination. Some combination of exercise, rest, medication, joint protection, physical and occupation therapy, and surgery is also used to treat RA patients.

RA is characterized by striking age-sex disparities. The incidence of RA in women increases steadily from the age of menarche to its maximal incidence around menopause. The disease is uncommon in men under age 45, but its incidence increases rapidly in older men and eventually approaches the incidence in women. These observations strongly suggest that androgens may play some role in RA. Dehydroepiandrosterone (DHEA), an adrenal product, is the major androgen precursor in men and women. Its production is dependent upon age, zig in the $2^{nd}$ and $3^{rd}$ decades in women. DHEA levels are low in both men and women with RA, and recent data show that levels of this hormone may be depressed before onset of the disease. The menopausal peak of RA onset suggests estrogen and/or progesterone deficiency may also play a role in the disease. RA typically remits during pregnancy, in parallel with increasing levels of corticosteroids, estrogens and progesterone. Oral contraceptives, which generate a condition of pseudopregnancy, also decrease the risk of RA. These data argue that adrenal and gonadal steroid hormones affect the development of RA. In addition, several studies indicate that corticosteroid production is inappropriately low in patients with RA.

Traditional treatment regimens for arthritis, including medications for reducing tissue inflammation, often meet with limited success. Hence, the search continues for alternative treatments for arthritis patients.

SUMMARY OF THE INVENTION

The invention is directed to the prophylactic, ameliorative and curative treatment of arthritis by administering Δ5-androstene-3β-ol-7,17-dione and precursors thereof which are readily metabolized in vivo to Δ5-androstene-3β-ol-7,17-dione but essentially incapable of being metabolized to androgens, estrogens or dehydroepiandrosterone.

DETAILED DESCRIPTION OF THE INVENTION INCLUDING A BEST MODE

Arthritis can be treated by administering therapeutic amounts of Δ5-androstene-3β-ol-7,17 dione and precursors thereof which are readily metabolized in vivo to Δ5-androstene-3β-ol-7,17-dione but essentially incapable of being metabolized to androgens, estrogens or dehydroepiandrosterone, such as Δ5-androstene-3β-acetoxy-7,17-dione and other 3β esters thereof.

Such treatment can be prophylactic, ameliorative or curative in nature.

Δ5-Androstene-3β-ol-7,17-dione

Δ5-androstene-3β-ol-7,17-dione is a derivative of dehydroepiandrosterone (DHEA) which does not appreciably stimulate, increase or otherwise enhance the production of sex hormones. Δ5-androstene-3β-ol-7,17 dione is commercially available from a number of sources including Steraloids, Inc. of Wilton, N.H. A number of procedures are available for synthesizing Δ5-androstene-3β-ol-7,17 dione from DHEA, with one such procedure described in U.S. Pat. No. 5,296,481.

Precursors of Δ5-androstene-3β-ol-7,17-dione, other than DHEA, may also be usefully employed in the treatment of arthritis. Such precursors are readily metabolized in vivo to the active Δ5-androstene-3β-ol-7,17-dione. One example of such a metabolizable precursor is the commercially available Δ5-androstene-3β-acetyl-7,17-dione. The 3β-acetyl group is readily hydrolyzed in vivo by esterases located in the blood and various body tissue to produce the active Δ5-androstene-3β-ol-7,17-dione, and is believed to be less susceptible to oxidation at the 3-position during the manufacturing process relative to Δ5-androstene-3β-ol-7,17-dione.

Administration

Administration Route

The Δ5 Androstene-3β-acetoxy-7,17-dione can be administered by virtually any of the commonly accepted practices for the administration of pharmaceutical preparations including specifically, but not exclusively, intravenous injection, mucosal administration, oral consumption, ocular administration, subcutaneous injection, transdermal administration, etc.

Mucosal administration of Δ5 Androstene-3β-acetoxy-7, 17-dione includes such routes as buccal, endotracheal, inhalation, nasal, pharyngeal, rectal, sublingual, vaginal, etc. For administration through the buccal/inhalation/sublingual/pharyngeal/endotracheal mucosa, the steroid may be formulated as an emulsion, gum, lozenge, spray, tablet or an inclusion complex such as cyclodextrin inclusion complexes. Nasal administration is conveniently conducted through the use of a sniffing powder or nasal spray. For rectal and vaginal administration the steroid may be formulated as a cream, douch, enema or suppository.

Oral consumption of the steroid may be effected by incorporating the steroid into a food or drink, or formulating the steroid into a chewable or swallowable tablet or capsule.

Ocular administration may be effected by incorporating the steroid into a solution or suspension adapted for ocular application such as drops or sprays.

Intravenous and subcutaneous administration involves incorporating the steroid into a pharmaceutically acceptable and injectable carrier.

For transdermal administration, the steroid may be conveniently incorporated into a lipophilic carrier and formulated as a topical creme or in an adhesive patch.

Dose Rate

The range of dosages and dose rates effective for achieving the desired biological properties and characteristics may be determined in accordance with standard industry practices. These ranges can be expected to differ depending upon whether the desired response is the prophylactic, ameliorative or curative treatment of arthritis, the specific type of arthritis and the severity of symptoms.

EXPERIMENTAL

Experiment 1

(Preparation of Δ5 Androstene-3β-acetoxy-7,17-dione)

Step One:

(Preparation of Δ5 Androstene-3-acetoxy-17-one)

A suitable, three-necked, round-bottom flask equipped with an overhead stirrer, reflux condenser, solids addition funnel and 110-volt temperature controller was charged with a mixture of dichloromethane (90 ml), glacial acetic acid (150 ml), and acetic anhydride (250 ml). To the mixture was added dehydroepiandrosterone (0.20 moles) purchased from Steraloids, Inc. of Wilton, N.H. The mixture was stirred to dissolve the solid dehydroepiandrosterone, and anhydrous sodium acetate (35.0 g) added. The resulting mixture was heated at 75° C. with stirring for 3 hours to complete the reaction.

The reaction mixture was poured into one liter of water and the resulting slurry stirred at room temperature for 2 hours. The organic dichloromethane layer was separated from the aqueous layer, and the aqueous layer extracted once with 50 ml of fresh dichloromethane. The combined organic dichloromethane extract was washed with water, saturated sodium bicarbonate solution (until neutral), and water. The resulting washed organic dichloromethane extract was evaporated under reduced pressure to a volume of 40 ml. Methanol (100 ml) was added to this concentrated extract and the resulting solid mass was cooled at 0° C. in a refrigerator for 2 hours.

The resulting solid white product was collected by vacuum filtration on a Buchner funnel and the filter cake air dried on the funnel to form a first crop of product weighing 50.5 g. The filtrate mother liquor was concentrated by evaporation under reduced pressure, and cooled at 0° C. in a refrigerator. The resulting solid white product was collected by vacuum filtration on a Buchner funnel and the filter cake air dried on the funnel to form a second crop of product weighing 10.2 g. The filtrate mother liquor from the second crop of product was diluted with water and the mixture was cooled at 0° C. in a refrigerator. The resulting solid white product was collected by vacuum filtration on a Buchner funnel and the filter cake air dried on the funnel to form a third crop of product weighing 4.2 g.

The first, second and third crops of product were combined to produce a total of 64.9 grams of Δ5 androstene-3-acetoxy-17-one.

Theoretical yield=66.1 g

First crop yield=50.5 g (76.4%)

Second crop yield=10.2 g (15.4%)

Third crop yield=4.2 g (6.4%)

Step Two:

(Preparation of Crude Δ5 Androstene-3-acetoxy-7,17-dione)

A suitable, three-necked, round-bottom flask equipped with an overhead stirrer, reflux condenser, addition funnel, thermometer, mineral oil filled bubbler and a gas inlet tube connected to a nitrogen cylinder, was charged with acetone (3.5 L) and cyclohexane (3.5 L). 1.51 moles of the Δ5 Androstene-3-acetoxy-17-one prepared in Step One was added to the flask with stirring to dissolved the solid Δ5 Androstene-3-acetoxy-17-one. 2.48 moles of solid sodium metaperiodate and water (1.1 L) were added to the stirred solution. 14.75 moles of a 70% aqueous solution of t-butyl hydroperoxide (2.0 L) was added to the flask through the addition funnel over a one-half hour period.

Over the first hour, the reaction mixture temperature rose from 20° C. to 32° C. Tap water was added to an external cooling bath and the reaction mixture temperature returned to 20° C. The reaction mixture was constantly vigorously stirred throughout the experiment, and the reaction judged to be complete after 48 hours by TLC monitoring of the disappearance of starting material. The mixture changed from a white slurry to a light yellow slurry over the course of the reaction.

The reaction mixture was poured into a stirred ice/water mixture (12 kg ice and 8 L water). Potassium sulfite (3 L of a 45% aqueous solution) was then added to the diluted reaction mixture over 30 minutes (100 mL/min) to destroy any remaining oxidant. The diluted mixture was stirred for an additional 2 hours, with ice added as needed to maintain the mixture at 15° C.

The resulting diluted, cooled reaction mixture was transferred to a suitable container and ethyl acetate (3 L) was added to dissolve and extract the product. The resultant mixture was stirred for one-half hour and then allowed to stand so as to permit the organic and aqueous layers to separate. The aqueous layer was examined by TLC, found to contain no product, and discarded. The solids containing organic layer was transferred to a separatory funnel, washed with water (3×1.5 L), then washed with a saturated salt solution (1×1.5 L). The washed organic layer was dried over sodium sulfate (300 g), with decolorizing carbon (100 g) added. The resulting organic slurry was filtered through a ceramic Buchner funnel containing a 0.5 inch Celite pad (100 g). The filter cake was washed with ethyl acetate (2×150 ml) and the washing combined with the filtrate.

The combined organic filtrate was concentrated in vacuo to near dryness to produce an off-white semi-solid. The semi-solid was suspended in methanol (400 ml) and again concentrated in vacuo to near dryness to produce a semi-solid. The semi-solid was slurried in methanol (600 ml) and the slurry stirred for 2 hours at ambient temperature. The solid product was collected by filtration on a ceramic Buchner funnel, and the solids washed with cold (5° C.) methanol (2×75 ml). The solid product was dried at 65° C. for 48 hours under high vacuum (<1 mm Hg vacuum). The process yielded 232 grams of crude solid Δ5 Androstene-3-acetoxy-7,17-dione.

Theoretical yield=521 g

Actual yield=232 g (44.5%)

Step Three:

(Preparation of Purified Δ5 Androstene-3-acetoxy-7,17-dione)

Method A

A 500 ml round bottom flask equipped with a magnetic stirrer was charged with 25.0 grams of the crude Δ5 Androstene-3-acetoxy-7,17-dione prepared in Step Two and 300 ml of a mixture of methanol and ethyl acetate (1:1, v/v). The magnetic stirrer was activated and the slurry stirred at room temperature until the crude Δ5 Androstene-3-acetoxy-7,17-dione was completely dissolved in the solvent mixture to form a first solution. A freshly prepared 10% aqueous solution of sodium bicarbonate (25 ml) was added over 10 minutes to the reaction mixture. The resulting milky mass was stirred at room temperature for 2.5 hours.

The reaction mixture was concentrated at room temperature under reduced pressure to 100 ml volume. The concentrated reaction mixture was diluted with 200 ml of ice water and stirred for 30 minutes at 0–5° C. The precipitated solids were collected on a ceramic Buchner funnel, and the aqueous filtrate reserved for additional product recovery. The solids on the funnel were washed with water (until neutral), and methanol (2×30 ml), with the methanol washing also reserved for product recovery. The first crop of solids was dried overnight under vacuum to give 18.0 g of purified product.

The aqueous filtrate from the first crop of solids was extracted with ethyl acetate (100 ml), and the separated organic extract was washed with water. The solvent of the washed extract was removed under reduced pressure to produce a solid product. This solid product was dissolved in the methanol washing from the first crop of solids, and the solution concentrated to 30 ml volume. Upon cooling the concentrate, a solid precipitate product formed which was collected by vacuum filtration. The second crop of solids was air dried to give 5.2 g of purified product.

The mother liquor filtrate from the second crop of solids was diluted with water and cooled. The resulting white solid precipitate was collected by vacuum filtration, and dried overnight at room temperature to give a third crop of 1.0 g of purified product.

The process yielded a total of 24.2 grams of purified solid Δ5 Androstene-3-acetoxy-7,17-dione.

Theoretical recovery=25.0 g

Actual recovery=24.2 g (96.8%)

Method B

A suitable round bottom flask equipped with a magnetic stirrer was charged with 1.0 gram of the crude Δ5 Androstene-3-acetoxy-7,17-dione prepared in Step Two and 10 ml of acetone. The magnetic stirrer was activated and the slurry was stirred at room temperature until the crude Δ5 Androstene-3-acetoxy-7,17-dione was completely dissolved in the acetone. To this solution was added 2.0 g of aluminum oxide basic. The resulting slurry was stirred at room temperature for 1 hour, then filtered through a bed of Celite. The collected solids and Celite bed were washed once with 5 ml of acetone, and the washing combined with the filtrate. The combined filtrate was evaporated to near dryness under reduced pressure to produce a solid product. The solid product was dissolved in a mixture of methanol and isopropyl ether (8:2, v/v) with heating. This solution was cooled at 0–5° C. for 30 minutes, resulting in precipitation of a white product. The precipitated solid was collected by vacuum filtration and air dried to give 0.9 grams of purified solid Δ5 androstene-3-acetoxy-7,17-dione.

Theoretical recovery=1.0 g

Actual recovery=0.9 g (90.0%)

I claim:

1. A method of treating rheumatoid arthritis, osteoarthritis, or fibromyalgia in a patient in need of such treatment, comprising administering to said patient a steroid selected from the group consisting of Δ5-androstene-3β-ol-7,17-dione and 3β esters thereof, wherein said administration results in amelioration or prevention of one or more symptoms of arthritis.

2. The method of claim 1, wherein said steroid is Δ5-androstene-3β-acetoxy-7,17-dione.

3. The method of either one of claims 1 and 2 wherein said patient is human.

4. The method of claim 3, wherein said patient is afflicted with osteoarthritis.

5. The method of claim 3, wherein said patient is afflicted with fibromyalgia.

6. The method of claim 3, wherein said patient is afflicted with rheumatoid arthritis.

7. The method of claim 3, wherein said patient is afflicted with an arthritis-related tissue inflammation symptoms.

8. The method of claim 3, wherein said patient is diagnosed with osteoarthritis.

9. The method of claim 3, wherein said patient is diagnosed with fibromyalgia.

10. The method of claim 3, wherein said patient is diagnosed with rheumatoid arthritis.

11. The method of claim 3, wherein said patient is diagnosed with an arthritis-related tissue inflammation symptoms.

12. The method of either one of claims 1 and 2, wherein said one or more symptoms of arthritis are selected from the group consisting of arthritis-related tissue inflammation, joint pain, joint stiffness, inability to move a joint normally, nodules, and swelling.

13. The method of claim 12, wherein said patient is afflicted with osteoarthritis.

14. The method of claim 12, wherein said patient is afflicted with fibromyalgia.

15. The method of claim 12, wherein said patient is afflicted with rheumatoid arthritis.

16. The method of claim 12, wherein said arthritis-related tissue inflammation is selected from the group consisting of connective tissue inflammation, joint inflammation, and synovium inflammation.

17. The method of claim 12, wherein said patient is diagnosed with osteoarthritis.

18. The method of claim 12, wherein said patient is diagnosed with fibromyalgia.

19. The method of claim 12, wherein said patient is diagnosed with rheumatoid arthritis.

20. The method of claim 3, wherein said steroid is administered by the route selected from the group consisting of intravenous injection, mucosal administration, oral consumption, ocular administration, subcutaneous injection, and transdermal administration.

21. The method of claim 20, wherein said mucosal administration includes routes selected from the group consisting of buccal, endotracheal, inhalation, nasal, pharyngeal, rectal, sublingual and vaginal.

* * * * *